(12) United States Patent
Senarith et al.

(10) Patent No.: US 10,039,912 B2
(45) Date of Patent: Aug. 7, 2018

(54) SYSTEM AND METHOD FOR COUPLING A TUBE WITH A MEDICAL DEVICE HANDLE

(71) Applicant: St. Jude Medical, Atrial Fibrillation Division, Inc., St. Paul, MN (US)

(72) Inventors: Patrick Senarith, Tustin, CA (US); James V. Kauphusman, Champlin, MN (US); Asim Syed, Irvine, CA (US); Terry Sterrett, Huntington Beach, CA (US); Kirk Wu, Walnut, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 306 days.

(21) Appl. No.: 13/840,196

(22) Filed: Mar. 15, 2013

(65) Prior Publication Data

US 2014/0018749 A1 Jan. 16, 2014

Related U.S. Application Data

(60) Provisional application No. 61/670,081, filed on Jul. 10, 2012.

(51) Int. Cl.

| A61M 39/10 | (2006.01) |
|---|---|
| A61M 25/00 | (2006.01) |
| A61M 25/01 | (2006.01) |
| A61B 18/14 | (2006.01) |
| A61B 5/042 | (2006.01) |
| A61M 25/09 | (2006.01) |
| A61B 34/20 | (2016.01) |

(52) U.S. Cl.
CPC ........ A61M 39/10 (2013.01); A61M 25/0009 (2013.01); A61M 25/0097 (2013.01); A61M 25/0136 (2013.01); *A61B 5/0422* (2013.01); *A61B 18/1492* (2013.01); *A61B 2034/2051* (2016.02); *A61M 2025/09116* (2013.01); *A61M 2039/1094* (2013.01)

(58) Field of Classification Search
CPC .......... A61M 25/0136; A61M 25/0097; A61M 39/10; A61M 25/0009
USPC .......... 604/167.01–167.06, 264, 533; 606/32
See application file for complete search history.

(56) References Cited

U.S. PATENT DOCUMENTS

| 4,003,382 | A | * | 1/1977 | Dyke ............................ 604/103 |
|---|---|---|---|---|
| 4,402,682 | A | * | 9/1983 | Garver et al. ................ 604/111 |
| 4,682,981 | A | * | 7/1987 | Suzuki et al. ................ 604/158 |
| 4,791,912 | A | | 12/1988 | Tashiro |
| 5,505,686 | A | | 4/1996 | Willis et al. |
| 5,782,828 | A | | 7/1998 | Chen et al. |
| 6,572,586 | B1 | * | 6/2003 | Wojcik ..................... 604/165.01 |

(Continued)

FOREIGN PATENT DOCUMENTS

| CN | 1668348 A | 9/2005 |
|---|---|---|
| JP | 2000-245851 A | 9/2000 |
| WO | 2011140583 A1 | 11/2011 |

*Primary Examiner* — Theodore Stigell
(74) *Attorney, Agent, or Firm* — Dykema Gossett PLLC (57) ABSTRACT

An elongate medical device handle may comprise a body defining an interior, an exterior, and a connector port extending between the interior and the exterior and defining an axis. The connector port comprises a portion having a polygonal cross-section taken transverse to the axis. In an embodiment, the polygonal cross-section may comprise a star shape. In an embodiment, a connector, such as a fluid connector, may be secured in the connector port using an adhesive.

17 Claims, 8 Drawing Sheets

(56) References Cited

U.S. PATENT DOCUMENTS

| | | | |
|---|---|---|---|
| 7,025,747 B2* | 4/2006 | Smith | 604/167.06 |
| 2002/0099360 A1 | 7/2002 | Bierman | |
| 2005/0234499 A1* | 10/2005 | Olson et al. | 606/192 |
| 2008/0249522 A1 | 10/2008 | Pappone et al. | |
| 2009/0099552 A1 | 4/2009 | Levy et al. | |
| 2010/0217189 A1* | 8/2010 | Pepper | 604/99.04 |
| 2010/0268163 A1* | 10/2010 | Rowe et al. | 604/167.03 |

* cited by examiner

SYSTEM AND METHOD FOR COUPLING A TUBE WITH A MEDICAL DEVICE HANDLE

CROSS-REFERENCE TO RELATED APPLICATION

This application claims the benefit of U.S. provisional application No. 61/670,081, filed 10 Jul. 2012, which is hereby incorporated by reference in its entirety as though fully set forth herein.

BACKGROUND a. Technical Field

The instant disclosure relates to medical devices, including handles for elongate medical devices.

b. Background Art

It is known to use elongate medical devices, such as, for example, catheters and sheaths or introducers, when performing various therapeutic and/or diagnostic medical procedures on or in various anatomical structures of a patient's body, such as, for example, the heart. Such devices generally include an elongate shaft having a proximal end portion, a distal end portion, a number of electrical and fluid elements, and a handle assembly disposed at the proximal end portion of the shaft. In order to provide access to the electrical and fluid elements in the shaft, the handle assembly generally includes one or more connector ports through which one or more connectors may provide connections to fluid supplies, mapping and navigation systems, and the like.

In some known medical device handles, a connector may move in a port, and the components on the interior of the handle to which the connector is coupled (such as, for example, a fluid lumen or an electrical wire) may twist or stretch. This movement of a connector and/or interior components may have undesirable effects, such as leakage of irrigation fluid due to crimping of an internal fluid lumen and/or separation of a connector from its connector port.

The foregoing discussion is intended only to illustrate the present field and should not be taken as a disavowal of claim scope.

BRIEF SUMMARY

To address one or more of the problems set forth above, an embodiment of an elongate medical device handle assembly may comprise a body defining an interior, an exterior, and a connector port. The connector port may extend between the interior and the exterior and may define an axis that extends from the interior to the exterior. The connector port may comprise a portion having a substantially polygonal cross-section taken transverse to the axis.

A method for manufacturing a medical device handle assembly that addresses one or more of the problems set forth above may include a number of steps. A first step may include providing a handle portion, the handle portion at least partially defining an interior of the handle and having an exterior, the handle portion comprising a connector port extending between the interior and the exterior and defining an axis that extends from the interior to the exterior. The connector port may comprise a substantially polygonal cross-section taken transverse to the axis. A second step may include coupling a connector with the connector port. In an embodiment, the method may further comprise treating the connector port before coupling the connector with the connector port. The treatment may include a plasma treatment and/or an abrasion treatment.

A method for facilitating access with a medical device handle assembly that addresses one or more of the problems set forth above may include a number of steps. A first step may include constructing a connector port having a polygonal cross-section taken substantially transverse to an axis of the connector port. A second step may include arranging the connector port in a handle portion of the medical device handle assembly to enable access between an interior and exterior of the handle portion along the axis of the connector port. A third step may include facilitating receipt of a connector via the polygonal cross-section of the connector port.

DETAILED DESCRIPTION

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
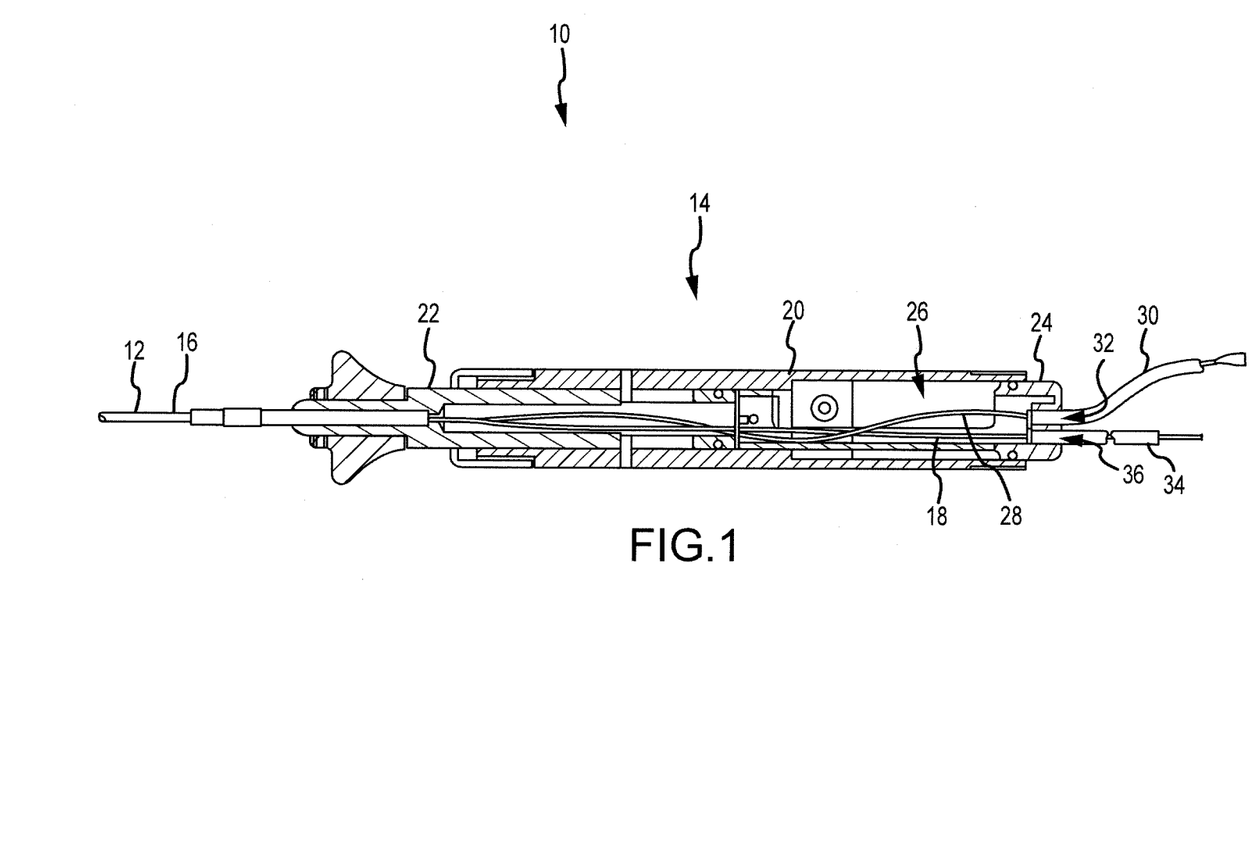
FIG. 1 is a cross-sectional view of a catheter handle.

Referring now to the figures, in which like reference numerals refer to the same or similar features in the various views, FIG. 1 is a longitudinal cross-sectional view of an embodiment of an elongate medical device 10. The medical device 10 may be one of many types known in the art such as, for example only, a catheter or a sheath. For ease of description, the medical device will be referred to as a catheter 10, though it is not so limited.

The catheter 10 may include an elongate shaft 12 (only a portion of which is shown) and a handle assembly 14. The handle assembly 14 may be used to guide the shaft 12 to a desired location within a patient to perform a desired procedure such as, for example, an ablation procedure, an electrophysiology (EP) mapping procedure, and/or a geometry mapping procedure. Accordingly, the catheter 10 may be coupled to a mapping and navigation system (not shown). Exemplary mapping and navigation systems are illustrated and described in U.S. patent application Ser. No. 13/231,284, which is hereby incorporated by reference in its entirety.

The shaft 12 may extend between a proximal end 16 and a distal end (not shown) and may include a number of features to enable the shaft to be guided to a particular location and to perform one or more procedures. For deflection and steering, the shaft 12 may include one or more control elements (not shown), such as shape memory wires and/or pull wires. For location and orientation detection, the shaft 12 may include one or more sensors (not shown), such as electrodes and/or electromagnetic coils, that may be electrically coupled to one or more visualization, mapping, and navigation systems known in the art. Such sensors may also be used for mapping the geometry of one or more anatomical features, such as a chamber of the heart. Electrodes (not shown) may also be provided for collection of other data, such as EP data for creating an EP map of an organ, such as the heart. The same or additional electrodes may also be provided for therapeutic purposes, such as for the delivery of ablation energy.

In an embodiment, the shaft 12 may also include a number of fluid features to, for example, irrigate an ablation tip to, e.g., minimize coagulum formation during delivery of ablation energy. For example, the shaft 12 may include one or more fluid lumens 18 extending from the handle assembly 14 to the distal tip of the shaft 12. In an open irrigation embodiment, the shaft 12 may also include one or more fluid ports, manifolds, and other features (not shown) for directing irrigation fluid over or near the surface of one or more ablation electrodes. Examples of such irrigation features may be found in United States patent application publication no. 2008/0249522 A1, which is hereby incorporated by reference as though set forth herein in its entirety.

The handle assembly 14 may include an outer body portion 20, a distal interior handle portion 22, and a proximal interior handle portion 24 (which may simply be referred to as the "proximal portion 24") collectively defining an interior 26 and having an exterior. Two or more of the handle body portions 20, 22, 24 may move relative to one another to, for example, actuate one or more pull wires for deflecting or steering a portion, such as a distal portion, of the shaft. For example, in one embodiment, distal interior handle portion 22 may move linearly in a longitudinal direction (e.g., left and right on the page of FIG. 1) with respect to outer body portion 20 and proximal interior handle portion 24. Examples of such steering features may be found in U.S. Pat. No. 5,782,828, which is hereby incorporated by reference as though set forth herein in its entirety.

The handle assembly 14 may include one or more features for connecting electrical elements in the shaft 12 (e.g., position sensors and mapping and therapy electrodes) to the systems and components outside the catheter that enable the operation of the electrical elements (e.g., mapping and navigation systems, ablation generators). At least one electrical wire 28 may extend through the interior 26 to provide a connection between the electrical elements in the shaft and the exterior systems. The electrical wire 28 may be electrically coupled with an exterior electrical connection 30, which may be inserted into the proximal interior handle portion 24 through an electrical connector port 32. The exterior electrical connection 30 may comprise materials and construction known in the art, and may be secured in the electrical connector port 32 through techniques known in the art, such as friction fit and adhesives, for example. An embodiment of the electrical connector port 32 is shown in greater detail in FIGS. 3-12.

As briefly noted above, the handle assembly 14 may also include features for connecting fluid elements in the shaft 12 (e.g., fluid lumens and irrigation ports) to fluid sources disposed outside the catheter. For example, the interior fluid tube or lumen 18 may extend though the interior 26 and may be fluidly coupled with a fluid lumen in the shaft 12 (i.e., allowing fluid to flow therebetween) and may be fluidly coupled with and/or pass through an exterior fluid connector, such as an extension tube 34. The remainder of this disclosure will, for ease of description, refer to embodiments including the extension tube 34, but other connectors are within the spirit and scope of this disclosure.

The extension tube 34 may comprise a polymer known in the art, such as polyurethane or Pebax™, commercially available from Arkema, Inc. The extension tube 34 may additionally comprise braiding or another structural support layer or material, as known in the art. The extension tube 34 may be inserted into the proximal interior handle portion 24 through a fluid connector port 36 and may be secured within the fluid connector port 36 through friction fit, adhesives, as described in conjunction with FIGS. 2A-2C, or other techniques known in the art. If an adhesive is used, the adhesive may comprise a urethane-based adhesive, in an embodiment. Examples of urethane-based adhesives include Polycin™ and Vorite™, though other adhesives, including urethane-based adhesives, may additionally or alternatively be used. Embodiments of the fluid connector port 36 are shown in greater detail in FIGS. 3-12. Additionally, the proximal interior handle portion 22 may comprise a polymer known in the art, such as polyoxymethylene (POM) sold under the trade name Delrin® and commercially available from E. I. du Pont de Nemours and Company.

Figure 2A:
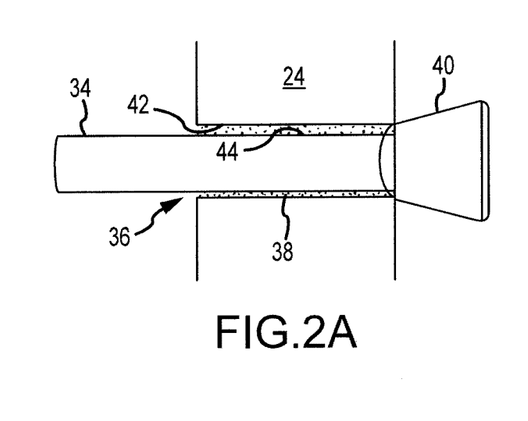
FIGS. 2A-2C are enlarged diagrammatic views of various embodiments of a portion of the catheter handle of FIG. 1.

FIG. 2A is an enlarged diagrammatic view of the coupling of an embodiment of the extension tube 34 with the fluid connector port 36. During assembly, one or more of the handle body portions, such as the proximal portion 24, may be joined with the fluid extension tube 34 which may be secured in place with an adhesive 38, such as a urethane-based adhesive, as mentioned above. That is, a surface 42 of the fluid connector port 36 may be bonded to a surface 44 of the extension tube 34. The fluid extension tube 34 may comprise, for example and without limitation, Pebax™ and/or another polymer and a braided layer, as noted above, and may proximally terminate in a luer connection 40. Coupling of the extension tube 34 and the fluid connector port 36 may be aided by a shape (i.e., a polygonal shape) of the fluid connector port 36 and/or by a treatment process, as described below.

Figure 2B:
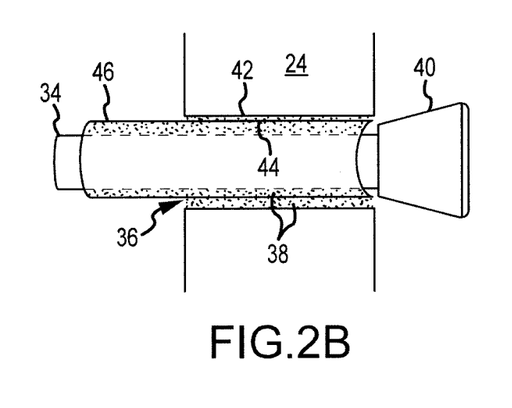

FIG. 2B is a diagrammatic view of a second embodiment of a coupling of the extension tube 34 with the fluid connector port 36. As shown in FIG. 2B, the extension tube 34 may be placed inside of a second tube 46. The second tube 46 may comprise, for example, a shrink tube. The extension tube 34 may be joined with the second tube 46 with additional adhesive 38, in an embodiment. The second tube 46 may be joined to the fluid connector port 36. Thus, the exterior of the second tube 46 may serve as the relevant surface (i.e., instead of the surface of the extension tube 34 itself) for bonding the extension tube 34 with the fluid connector port 36 (i.e., the surface to which a treatment process may be applied, as discussed in conjunction with FIG. 13).

Figure 2C:
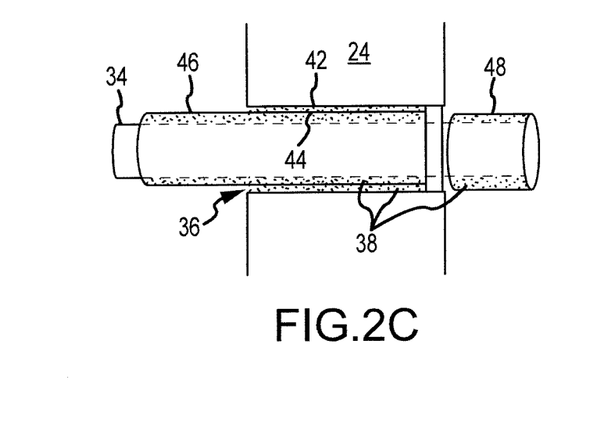

FIG. 2C is a diagrammatic view of a third embodiment of a coupling of the extension tube 34 with the fluid connector port 36. As shown in FIG. 2C, instead of a separate luer connector 40, the proximal end of the extension tube 34 may be disposed inside of a third tube 48 and joined to the third tube 48 with additional adhesive 38. The third tube 48 may comprise a shrink tube, in an embodiment.

Figure 3:
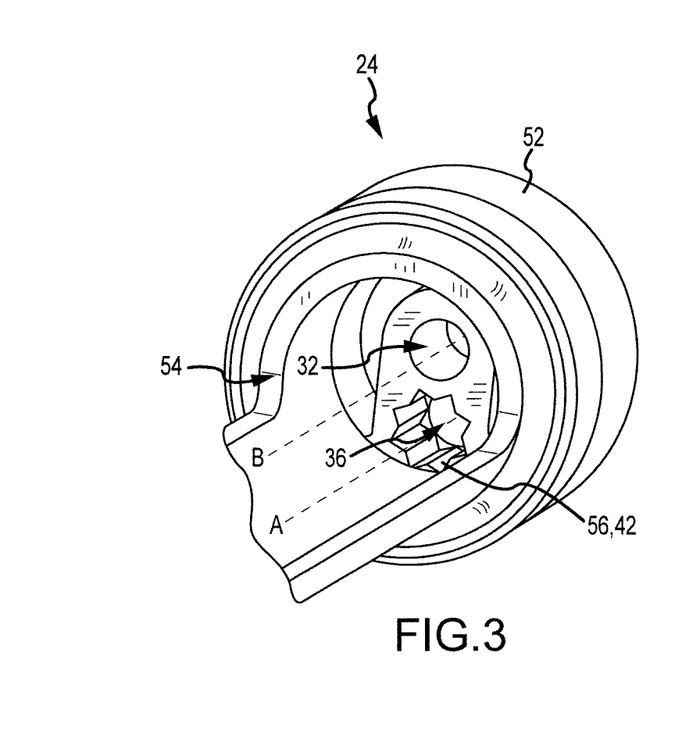
FIGS. 3 and 4 are isometric views of an embodiment of a portion of the catheter handle of FIG. 1.
Figure 4:
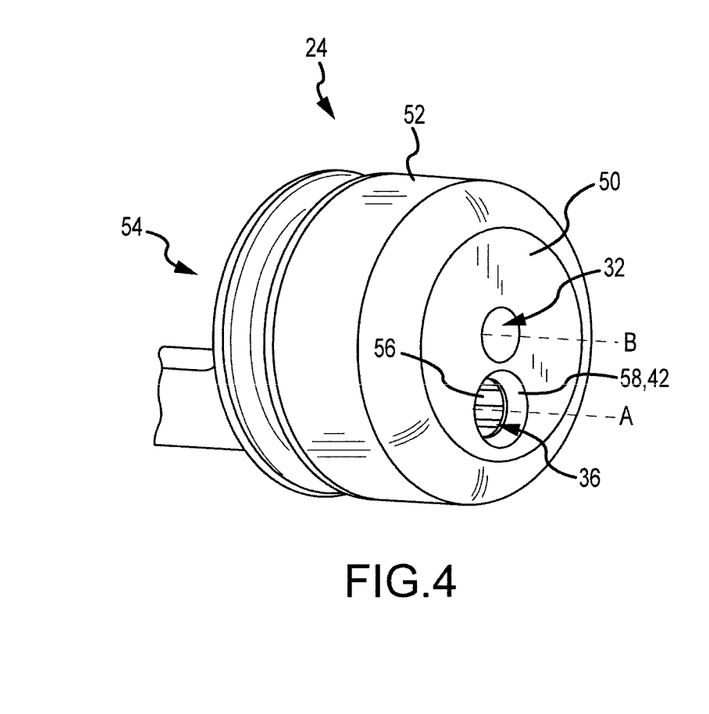
Figure 5:
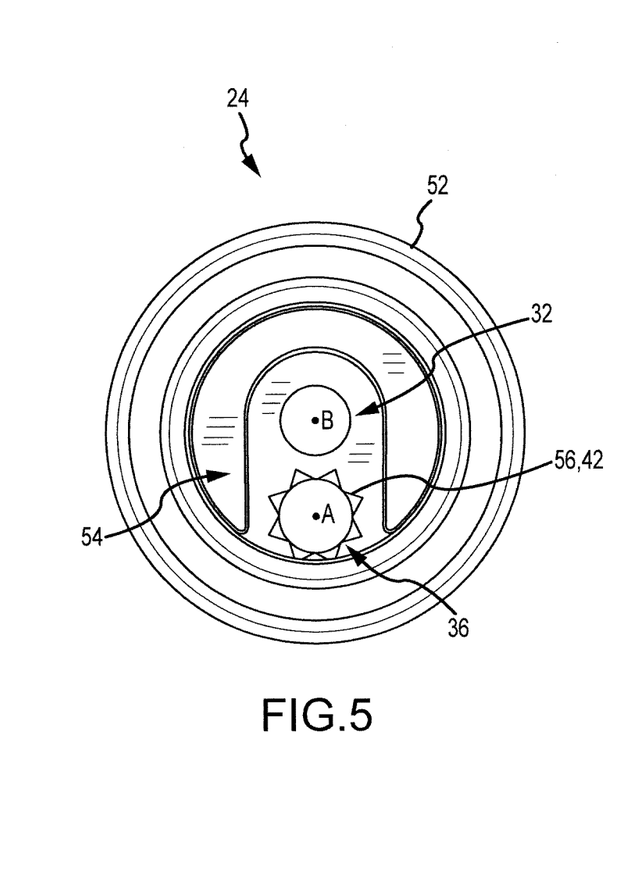
FIGS. 5 and 6 are opposing end views of the catheter handle portion of FIGS. 3 and 4.
Figure 6:
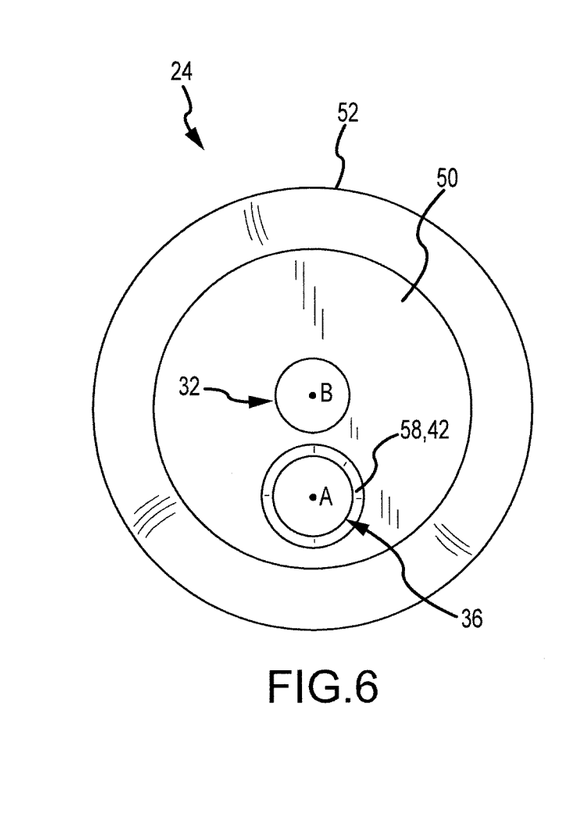

FIGS. 3 and 4 are isometric views of a portion of an embodiment of the proximal portion 24, and FIGS. 5 and 6 are opposing end views of the proximal portion 24. Referring to FIGS. 3-6, the proximal portion 24 may include a proximal exterior 50, a body 52 defining an interior 54, and a fluid connector port 36 and an electrical connector port 32 extending between the interior 54 and exterior 50. The fluid connector port 36 may define, extend along, and be generally radially symmetric about an axis A, and the electrical connection port 32 may define, extend along, and be generally radially symmetric about an axis B. The electrical connector port 32 may comprise a cylindrical passageway through a portion of the body 52 that is, a cross-section of the passageway, taken transverse to the axis B, may be substantially circular. In the embodiment shown, the electrical connector port 32 is disposed on the proximal end of the proximal portion 24, and thus would be on the proximal end of the handle assembly 14 itself. In an embodiment, the electrical connector port 32 may taper from interior to exterior or from exterior to interior.

Figure 10:
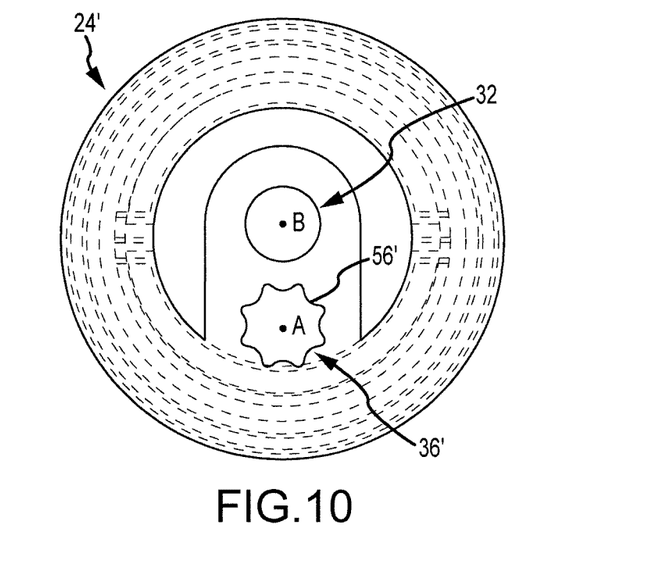
FIG. 10 is an enlarged cross-sectional view of a portion of the catheter handle portion of FIG. 8.
Figure 11:
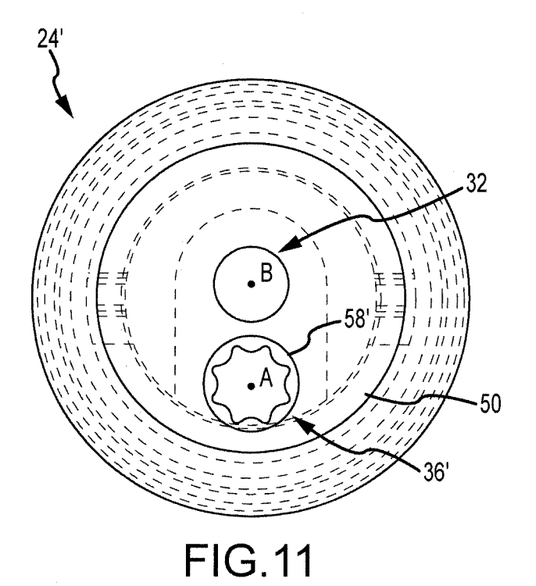
FIGS. 11 and 12 are opposing end views of the catheter handle portion of FIG. 7.
Figure 12:
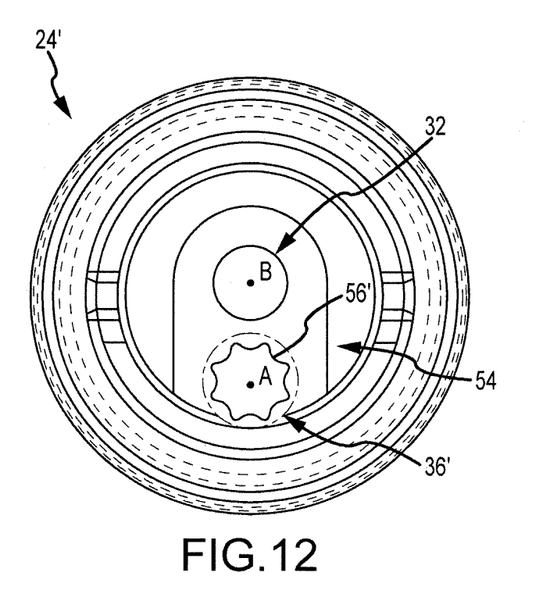

The fluid connector port 36 may comprise a polygonal passageway 56 through a portion of the body 52—that is, a cross-section of the passageway 56, taken transverse to the axis A, may be substantially polygonal. As shown, the polygon may comprise a plurality of sides between convex and/or concave vertices. In an embodiment, the polygon may comprise alternating convex and concave vertices, so as to form a star pattern. The polygonal portion 56 of the fluid connector port 36 may include any number of sides (e.g., at least four (4), six (6), eight (8), or more sides) and any suitable convex and/or concave polygonal shapes, such as a rectangle, hexagon, octagon, or other shape. One or more sides of the polygon may be straight, as shown in FIGS. 3-6, or arcuate, as shown in FIGS. 10-12. The polygonal portion 56 of the fluid connector port 36 may be tapered, in an embodiment, from interior to exterior or from exterior to interior. The fluid connector port 36 may further comprise a circular portion 58 disposed on the exterior—i.e., proximal—side of the polygonal portion 56. The circular portion 58 also may be tapered from interior to exterior or from exterior to interior, as shown. Alternatively, the circular portion 58 may comprise a counterbore.

As noted above, Delrin® POM and other materials may be difficult to adhesively bond due to low surface energy. Accordingly, the shape of the fluid connector port 36 may be configured such that a mechanical interlock forms when the adhesive cures therein and around the portion of the extension tube 34 disposed within the fluid connector port 36. In other words, the polygonal portion 56 of the fluid connector port 36 may provide more surface area for adhesive bonding than would a circular configuration, facilitating receipt of a fluid connector such as the extension tube 34 and allowing for a more secure coupling between the proximal portion 24 and a fluid connector such as the extension tube 34.

Figure 7:
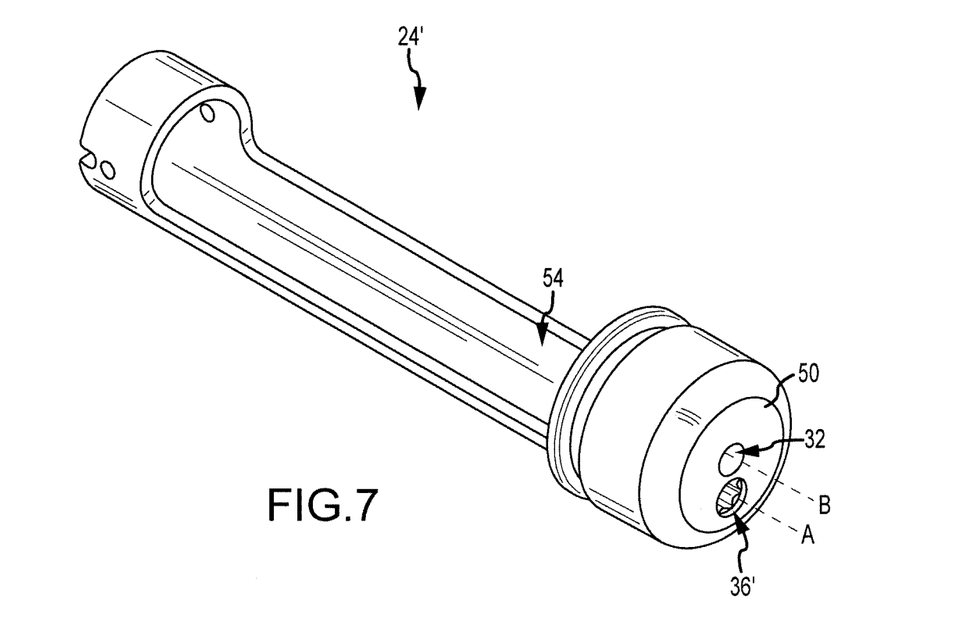
FIG. 7 is an isometric view of an embodiment of a portion of the catheter handle of FIG. 1.
Figure 8:
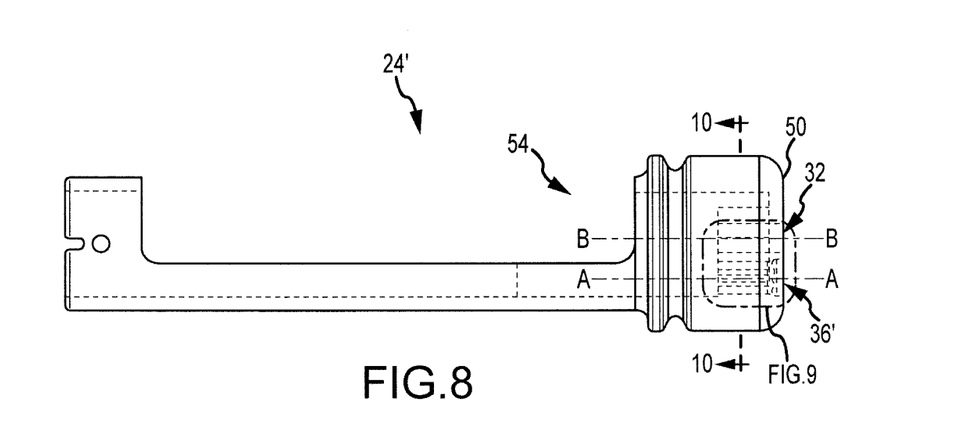
FIG. 8 is a side view of the catheter handle portion of FIG. 7.
Figure 9:
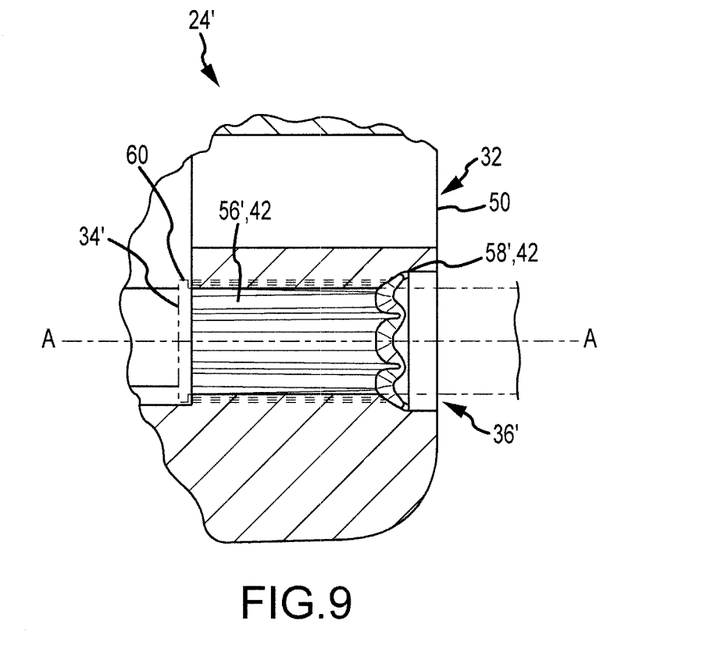
FIG. 9 is an enlarged view of a portion of FIG. 8, with a fluid connector additionally shown in phantom.

FIG. 7 is an isometric view of another embodiment of the proximal interior handle portion 24'. FIG. 8 is a side view of the proximal interior handle portion 24'. FIG. 9 is an enlarged cross-sectional view of a portion of the proximal interior handle portion 24', with an embodiment of the extension tube 34' additionally shown in phantom. FIG. 10 is a cross-sectional view of proximal interior handle portion 24'. Figured 11 and 12 are opposing end views of the proximal interior handle portion 24'. The proximal interior handle portion 24' is substantially the same as the proximal interior handle portion 24 illustrated in FIGS. 3-6, but the configuration of the fluid connector port 36' in FIGS. 7-12 is different from the fluid connector port 36 in FIGS. 3-6.

The fluid connector port 36' may include portion 56' having a polygonal cross-section with arcuate sides. In addition, the fluid connector port 36' may include a flared circular portion 58' on a proximal side of the port 36'. Furthermore, adhesive may be used to secure a connector in the fluid connector port 36', and the adhesive may be applied to the flared circular portion 58' of the port so as to form a flange that prevents a distal force on the fluid extension tube 34, 34' along the axis A from pushing the tube 34, 34' into the interior of the handle. The flared portion 58' of the fluid connector port 36' may, in an embodiment, include a cross-sectional shape that is substantially circular, as shown, or that is other than a circle.

As shown in FIG. 9, an embodiment of the extension tube 34' inserted through the port 36' may include a flange 60 to prevent a proximal force on the extension tube 34' along the axis A from pulling the tube 34' out of the handle. Such an extension tube 34' may also find use with the fluid connector port 36 shown in FIGS. 3-6 and other embodiments.

Figure 13:
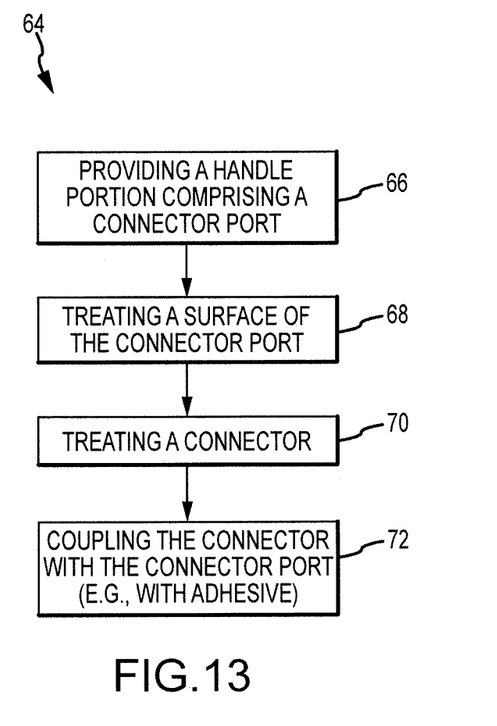
FIG. 13 is a flow chart illustrating an exemplary method of manufacturing a portion of a medical device handle assembly.

FIG. 13 is a flow chart illustrating a portion of an exemplary method 64 of manufacturing a medical device handle assembly. The method 64, along with other steps not detailed herein but known in the art, may be performed to manufacture an embodiment of the handle assembly 10 shown in FIG. 1. The method 64 will therefore be described with reference to the handle assembly 10 and handle portion embodiments 24, 24' illustrated in FIGS. 1-12. It should be understood, however, that the method is not limited to such handles and handle portions.

The method 64 may begin with a step 66 of constructing or otherwise providing a handle portion at least partially defining an interior of the handle and having an exterior. The handle portion may include a connector port extending between the interior and the exterior and defining an axis that extends from the interior to the exterior. The connector port may comprise a substantially polygonal cross-section taken transverse to the axis. The handle portion may be or may comprise, in embodiments, proximal portion 24 or proximal portion 24'.

The configuration of the fluid connector ports 36, 36' (e.g., the additional surface area provided by the polygonal portions 56, 56') may allow for a very strong mechanical interlock and thus may obviate the need for other steps or procedures for improving adhesive bonding, such as treating the fluid connector port 36 or extension tube 34, that may be necessary for other ports and connectors (such as known circular ports, for example). Accordingly, the fluid connector ports 36, 36' may allow for simpler manufacturing of a handle assembly than in known devices.

Although treatment may not be essential, the method 64 may continue to two treatment steps 68, 70, if desired. In other words, the treatment steps 68, 70 may be optional (i.e., one or both of the treatment steps 68, 70 may be omitted from some embodiments of the method 64). The treatment steps 68, 70 may include a step 68 of treating a surface of the connector port of the handle portion and a step 70 of treating a connector.

Referring to FIGS. 2A-2C and 13, because the surface energy of one or more materials comprising the proximal interior handle portion 22 (e.g., such as Delrin®) may have a relatively low surface energy, adhesive bonding may be improved by treating surfaces of the interior proximal handle portion 24, 24' before applying adhesive. Accordingly, in an embodiment, a surface 40 of the fluid connector port 36, 36' and/or a surface 42 of the fluid extension tube 34, 34' (or a surface of another tube or layer placed on the exterior of the fluid extension tube) may be treated to improve adhesion. One or both of a plasma treatment and an abrasion treatment, each of which is discussed below, may be applied, in embodiments of the treatment steps 68, 70, in addition to other known treatment processes.

For an adhesive to successfully wet and adhere to a bonding surface, the surface energy of the adhesive must be less than that of the surface to which the adhesive is intended to bond. As noted above, one or more materials comprising the interior handle portion 24, 24' may have relatively low surface energies, making adhesive bonding difficult.

A plasma treatment process may be applied to the bonding surface (e.g., surfaces 40, 42) to raise its surface energy to improve bonding by an adhesive. The plasma treatment process may include placing the interior handle portion 22 (or the extension tube 34, 34' and any exterior layers of materials) in a plasma treatment chamber (i.e., between an anode plate and a cathode plate in the chamber). An inert gas, such as nitrogen, may be introduced into the chamber. Energy may be delivered to the anode and cathode plates to cause the inert gas to ionize and form a plasma. The plasma may be used to react with or energetically scrub debris on the treated surface. The plasma may be used to form functional surface groups. The plasma treatment may occur at a relatively low temperature (e.g., room temperature) and may leave little to no residue or debris on the treated surface.

In addition to or as an alternative to plasma treating, the surface 40 of the fluid connector port 36, the surface 42 of the fluid extension tube, and/or other surfaces involved in bonding may be abrasion-treated. In an embodiment, an abrasion treatment process may involve the use of pneumatic energy to deliver abrasive media to the bonding surface(s). The abrasion may remove debris from the treated surface as well as some of the material comprising the surface, increasing the surface area of the surface. By removing debris and increasing surface area, the surface energy of the surface may be increased, improving adhesion. Depending on the abrasive media used and the other aspects of the treatment, cleaning may be required following abrasion treatment to remove debris from the treated surface and adjacent surfaces. Furthermore, masking may be required to prevent treatment of surfaces for which treatment is not desired. Accordingly, in embodiments, an abrasion treatment process may include masking surfaces of the interior handle portion 24, 24' besides the surface 40 of the port 36, 36', masking portions of the surface 42 of the extension tube 34, 34' and/or other surfaces, and may further include a cleaning step following the treatment.

Plasma and/or abrasion treatment processes, or other known treatment processes, may also be applied to the electrical connector port 32 and/or the exterior electrical connection 30 during manufacturing. Any adhesive 38 applied may also be subjected to a curing process to improve adhesion.

After treating, the method 64 may continue to a step 72 of coupling the connector with the connector port. The coupling step 72 may include, for example, inserting the connector into the connector port from the proximal or distal end of the connector port. The coupling step 72 may also include, in embodiments, applying an adhesive to one or more surfaces of the connector port, the connector, and/or other intervening materials or layers. Following the coupling step 72, the remainder of the handle assembly may be constructed according to known methods.

The design and construction of the handle assembly 14, and the proximal portions 24, 24' in particular, may lead to a more secure coupling between the fluid extension tube 34, 34' and the fluid connector port 36, 36' than in known designs. The proximal portions 24, 24' may also allow for simpler manufacturing than known designs. In particular, the polygonal cross-section of the fluid connector port 36, 36' provides ample surface area for adhesive to adhere and, in conjunction with cured or dried adhesive therein, forms a mechanical interlock that also prevents or resists rotation of the fluid extension tube 34, 34' within the port 36, 36'. Also, the use of a urethane-based adhesive may be more reliable than presently-used adhesives. Moreover, the circular portion 58, 58' may serve as a reservoir or well for adhesive to pool and harden in something of a fillet or flared shape such that linear movement, e.g., in and out of the port 36, 36', may be prevented or resisted. Further, the various treating and curing processes that may be performed may also improve the strength of the bond between the fluid extension tube 34, 34' and the fluid connector port 36, 36'. As a result, the fluid extension tube 34, 34' may be securely held within the fluid connector port 36, 36' to prevent or resist twisting and stretching of components within the interior 26 of the handle assembly 14.

Although a number of embodiments have been described above with a certain degree of particularity, those skilled in the art could make numerous alterations to the disclosed embodiments without departing from the spirit or scope of this disclosure. For example, all joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An elongate medical device handle assembly comprising:
   a body comprising an outer body portion, a distal interior handle portion, and a proximal interior handle portion defining an interior, and having an exterior, and
   a connector port, said connector port comprising an open passageway that extends between said interior and said exterior and defines an axis that extends longitudinally from said interior to said exterior, wherein said passageway comprises a first axial portion having a substantially polygonal cross-section taken transverse to said axis and a second axial portion having a cross-sectional shape, taken transverse to said axis, that is different from said substantially polygonal cross-section;
   a connector with a connector proximal end and a connector distal end, the connector extending from said proximal interior handle portion to said exterior through said passageway where the connector distal end extends through the proximal interior handle portion into the interior, wherein said connector is coupled with a fluid lumen disposed in said interior where a fluid lumen volume is less than a volume of the interior.

2. The medical device handle assembly of claim 1, wherein said polygonal cross-section comprises at least eight sides.

3. The medical device handle assembly of claim 1, wherein said second axial portion is located closer to said exterior than is said polygonal cross-section portion.

4. The medical device handle assembly of claim 1, wherein said second axial portion comprises a flared or tapered portion.

5. The medical device handle assembly of claim 1, wherein said polygonal cross-section comprises a plurality of sides between a plurality of vertices, wherein said sides are curved.

6. The medical device handle assembly of claim 1, wherein said polygonal cross-section comprises a plurality of sides between a plurality of vertices, wherein said sides are straight.

7. The medical device assembly of claim 1, wherein said polygonal cross-section comprises a star shape.

8. The elongate medical device handle assembly of claim 1, wherein said cross-sectional shape of said second axial portion is substantially circular.

9. The elongate medical device handle assembly of claim 1, further comprising an adhesive affixing said connector to a surface of said first axial portion of said connector port.

10. The medical device handle assembly of claim 9, wherein said adhesive comprises a urethane-based adhesive.

11. The medical device handle assembly of claim 9, wherein said adhesive is cured.

12. A method for manufacturing a medical device handle assembly comprising:
    providing a handle portion for medical device handle assembly, the handle portion at least partially defining an interior of the handle and having an exterior, the handle portion comprising an outer body portion, a distal interior handle portion, a proximal interior handle portion, a connector port comprising a passageway that extends between the interior and the exterior and defines an axis that extends from the interior to the exterior, wherein the passageway is smaller than the interior and wherein the passageway comprises a first axial portion defining a substantially polygonal opening transverse to said axis and a second axial portion defining a substantially circular opening transverse to said axis; and
    coupling a connector with said connector port, wherein the connector includes a connector proximal end and a connector distal end, the connector extending from the proximal interior handle portion to the exterior and wherein said coupling comprises applying an adhesive between the connector and a surface of the first axial portion of the connector port.

13. The method of claim 12, further comprising treating the connector port before applying the adhesive.

14. The method of claim 13, wherein said treating comprises a plasma treatment.

15. The method of claim 13, wherein said treating comprises an abrasion treatment.

16. The method of claim 12, wherein said connector comprises a fluid conduit extending through said connector port along said axis.

17. A medical device handle assembly, comprising:
    a body comprising an outer body portion, a distal interior handle portion, and a proximal interior handle portion defining an interior, an exterior, and
    a connector port, said connector port comprising an opening that extends between said interior and said exterior and defines an axis that extends from said interior to said exterior, wherein said opening comprises a first axial portion having a plurality of sides, said plurality of sides defining a closed polygonal shape, and a second axial portion defining a closed, substantially circular shape;
    a tubular connector with a tubular connector proximal end and a tubular connector distal end extending through said opening from said interior to said exterior, where the tubular connector distal end extends through the proximal interior handle portion into the interior, wherein said tubular connector is coupled with a fluid lumen disposed in said interior where a fluid lumen volume is less than a volume of the interior; and an adhesive affixing said tubular connector to at least one of said sides of said first axial portion of said connector port.

* * * * *